(12) United States Patent
Elberg

(10) Patent No.: US 6,267,764 B1
(45) Date of Patent: Jul. 31, 2001

(54) OSTEOSYNTHESIS SYSTEM WITH ELASTIC DEFORMATION FOR SPINAL COLUMN

(75) Inventor: Jean-François Elberg, Paris (FR)

(73) Assignee: Stryker France S.A. (FR)

( * ) Notice: Subject to any disclaimer, the term of this patent is extended or adjusted under 35 U.S.C. 154(b) by 0 days.

(21) Appl. No.: 09/308,340
(22) PCT Filed: Nov. 13, 1997
(86) PCT No.: PCT/FR97/02037
§ 371 Date: May 14, 1999
§ 102(e) Date: May 14, 1999
(87) PCT Pub. No.: WO98/22033
PCT Pub. Date: May 28, 1998

(30) Foreign Application Priority Data

Nov. 15, 1996 (FR) .................................................. 96 13956

(51) Int. Cl.⁷ .................................................. A61B 17/56
(52) U.S. Cl. .................................................. 606/61; 606/63
(58) Field of Search .......................... 606/53–55, 57–58, 606/60–61, 63, 69; 623/17; 267/195, 153, 293

(56) References Cited

U.S. PATENT DOCUMENTS 5,415,661 * 5/1995 Holmes .................................. 606/69
5,480,401 * 1/1996 Navas .................................... 606/61
5,961,516 * 10/1999 Graf ...................................... 606/61

FOREIGN PATENT DOCUMENTS

| 0 667 127A | 8/1995 | (EP) | A61B/17/58 |
| 2717370 | * 9/1995 | (FR) | . |
| 2718946 | * 10/1995 | (FR) | . |
| WO94 21185A | 9/1994 | (WO) | A61B/17/58 |

* cited by examiner

Primary Examiner—Cary O'Connor
(74) Attorney, Agent, or Firm—Blakely Sokoloff Taylor & Zafman

(57) ABSTRACT

The osteosynthesis system has two anchor members (2) adapted to be fixed to two vertebrae (4), and a link member (6; 106) adapted to interconnect the anchor members and to exert stresses against the two anchor members moving towards each other in translation. The link member (6; 106) is elastically deformable in bending about a deformation axis (45, 47, 49). It has two fixing portions (16) adapted to be fixed to the two anchor members (2) and an intermediate portion (40). The intermediate portion is offset from an alignment axis (18) of the two fixing portions (16). The link member (6; 106) has two abutments (39) disposed so as to come into abutment against each other when the link member is deformed about the axis.

13 Claims, 2 Drawing Sheets

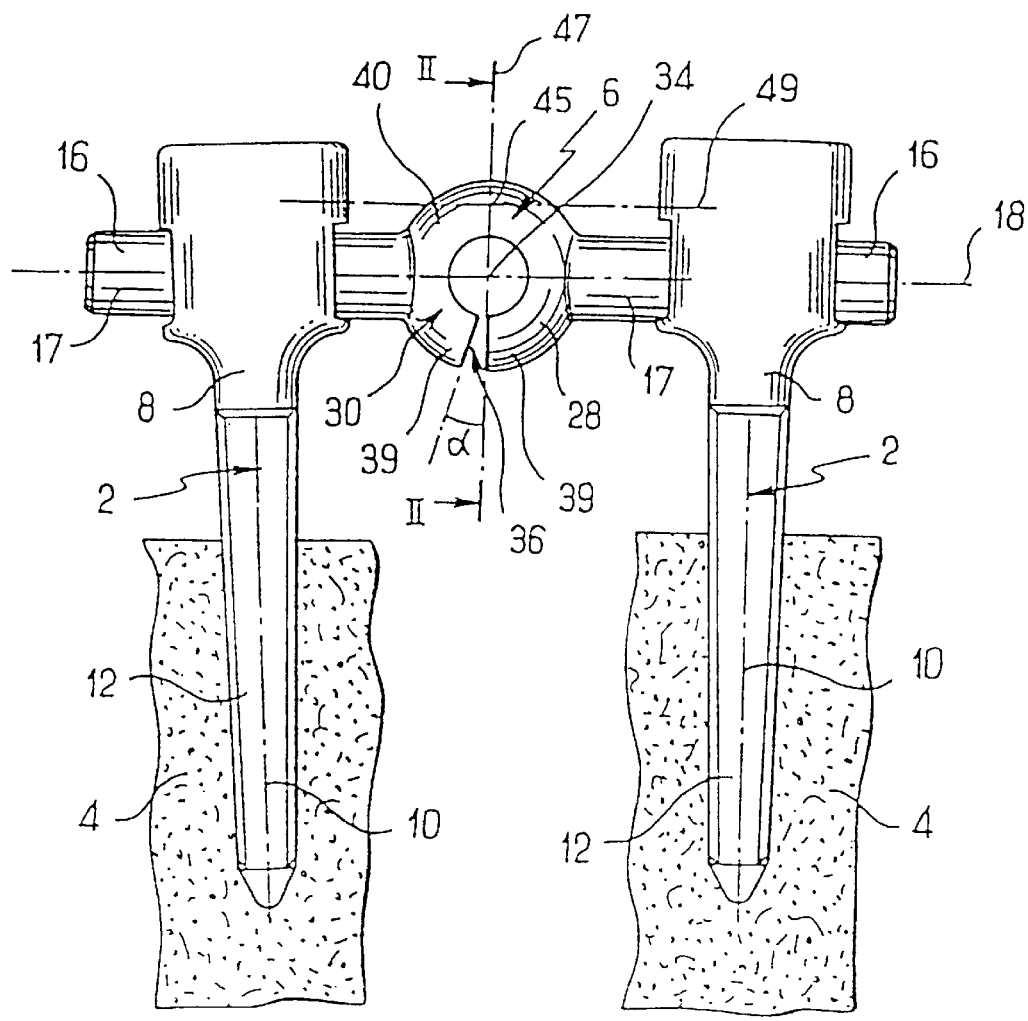
FIG_1
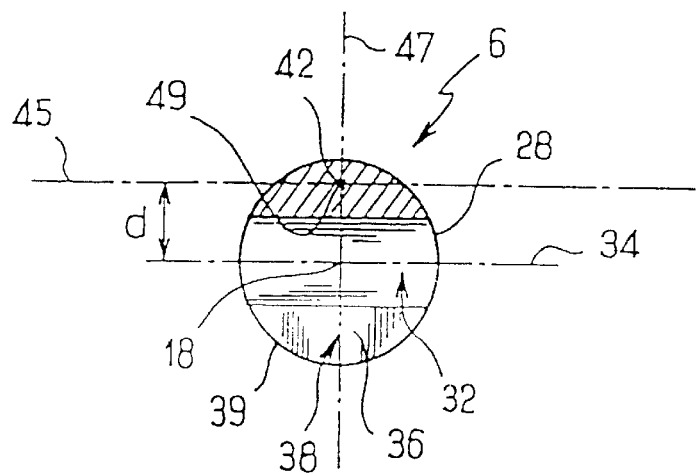
FIG_2

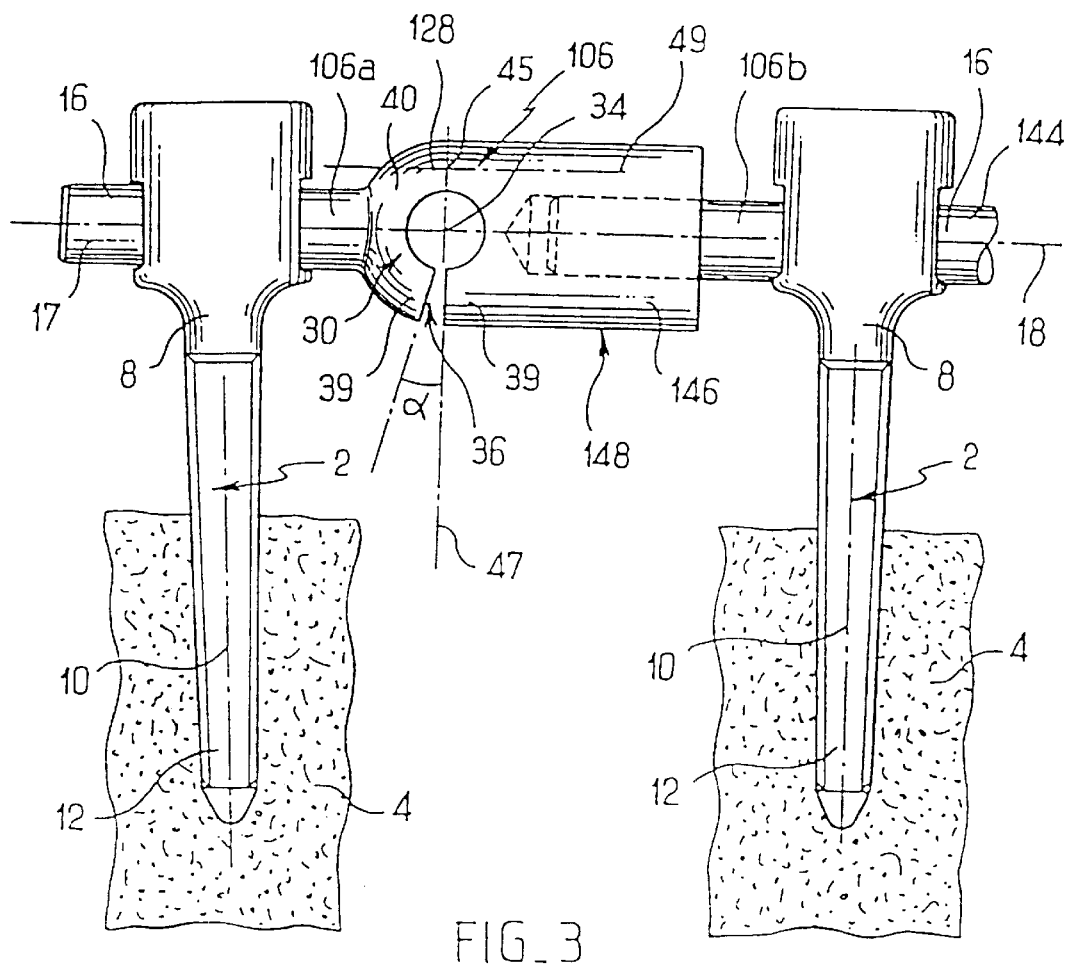
FIG_3
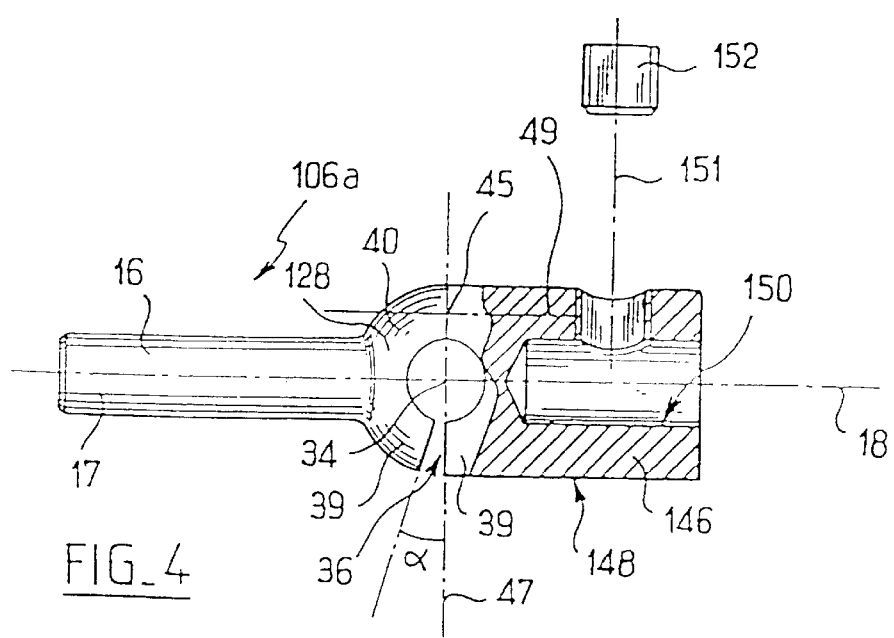
FIG_4

OSTEOSYNTHESIS SYSTEM WITH ELASTIC DEFORMATION FOR SPINAL COLUMN

BACKGROUND OF THE INVENTION

1. Field of the Invention

The present invention relates to osteosynthesis systems for the spinal column.

2. Description of Related Art

Document FR-2 659 546 discloses an osteosynthesis system for the spinal column or backbone which has anchor members for fixing to a series of vertebrae of the spine, and at least one rigid link element designed to interconnect the anchor members. Once the system has been fixed to a series of vertebrae and once it has been assembled, it constitutes a rigid device preventing the vertebrae from moving relative to one another. This rigidity enables the device to support all or part of the stresses instead of the series of vertebrae concerned. Nevertheless, the first vertebra adjacent to the series is quite free to move relative to the series of vertebrae made rigid. A sharp discontinuity in the distribution of stresses along the spine can then arise between the last vertebra of the series and the first free vertebra. Consequently, the disk between these two vertebrae is overtaxed, and indeed an abnormal increase in stresses is observed at the disk. Very often this accelerates degeneration of the disk. This can be referred to as the "new-hinge" syndrome.

Document WO 94/21185 presents an osteosynthesis device for the spinal column in which two pedicular screws are interconnected by a link member having a flexible central portion that is U-shaped and offset laterally. Thus, when the two vertebrae are subjected to stresses tending to displace the two anchor members in relative rotation about an deformation axis, the link member is itself subjected to a bending moment and it bends elastically about the deformation axis. It therefore supports these stresses in part. The system recreates in part the biomechanical organization of the functional unit made up of the two fixed vertebrae together with the intervertebral disk. Nevertheless, that device has the drawback that the possibility of relative rotation between the two pedicular screws is essentially a function of the elasticity of the intermediate portion. In other words, the suitability of the intermediate portion for deforming relies on said elasticity. Unfortunately, when said elasticity is high so as to restrict relative displacement, then the vertebrae can be subjected to high levels of stress which can be harmful to them. Conversely, when the elasticity is low, support provided to the vertebrae is mediocre.

BRIEF SUMMARY OF THE INVENTION

An object of the invention is to provide an osteosynthesis system enabling the deformation ability of the intermediate portion for deformation to be controlled without constraining the choice of elasticity.

To achieve this object, the invention provides an osteosynthesis system for the spinal column, the system comprising at least two anchor members adapted to be fixed to two vertebrae of the spinal column, and a link member adapted to interconnect the two anchor members and exerting stresses against movement of the two anchor members in translation towards each other, the link member being elastically deformable in bending about at least one deformation axis, the link member having at least two fixing portions adapted to be fixed to the two anchor members, and at least one intermediate portion such that the two fixing portions are connected to each other solely by the intermediate portion, the intermediate portion being offset from an alignment axis defined by the two fixing portions. For the or each intermediate portion, the link member further has two abutments facing each other and disposed so as to come into abutment against each other when the link member is deformed about the deformation axis, or at least one of the deformation axes, in a given direction of rotation and through an angle equal to a predetermined limit value.

Thus, the amplitude of the deformation of the link member in this direction of rotation is limited. The abutments thus serve to control the ability of the link member to deform without that having any influence on the elasticity selected for the intermediate portion.

When the system has three anchor members with two of the anchor members rigidly connected to each other and with two of the anchor members interconnected by the deformable link member and located at one end of the series, a rigidity or transition gradient is established between the rigid portion of the spine and its free portion. Consequently, a better distribution of stresses is obtained along the spine. This avoids the appearance of a sudden discontinuity in stress distribution between the last vertebra of the rigid series and the first free vertebra, and on the contrary, it is easier to obtain a harmonious distribution of stresses along the spine. In addition, when the system relates to two vertebrae only, a flexible arthrodesis is provided between those two vertebrae.

Advantageously, the deformation axis or at least one of the deformation axes extends perpendicularly to a longitudinal direction of each anchor member and to a longitudinal direction of the link member.

Advantageously, the deformation axis or at least one of the deformation axes extends substantially parallel to a longitudinal direction of each anchor member.

Advantageously, the deformation axis or at least one of the deformation axes extends parallel to a longitudinal direction of the link member.

Thus, each of these axes corresponds to an axis of relative displacement in rotation of the two anchor members relative to each other, because of the movement of the vertebrae. Depending on circumstances, the intervertebral disk is relieved at least in part of the stresses corresponding to said respective displacements.

Advantageously, the alignment axis lies between the intermediate portion and the two abutments.

Advantageously, the intermediate portion has an outer face of spherical shape.

Advantageously, each of the two abutments has an outer face of spherical shape.

Thus, in these two cases, since the system is designed to be located inside the body, the number of sharp edges is limited and the sharp edges are placed so as to reduce the risk of harm due to the presence of the system in the body of the patient.

Advantageously, the spherical face of the intermediate portion and the spherical faces of the two abutments have a common center of curvature.

Advantageously, for the or each pair of fixing portions, the link member has a junction part contiguous with the two fixing portions, the junction part associated with the or at least one of the pairs of fixing portions being a single piece.

Advantageously, for the or each pair of fixing portions, the link member has a junction part contiguous with the two fixing portions, the junction part associated with the, or at least one of the, pairs of fixing portions having first and second mutually distinct link elements and fixing means for fixing the first and second link elements together.

Thus, the link member is made easier to fabricate when the junction part is in two parts or the link member has a large number of two-part junction parts relative to the total number of junction parts.

Advantageously, the fixing means are adapted to enable the distance between the two associated anchor members to be adjusted in the longitudinal direction of the link member.

Thus, the length of the link member is adjustable. While the system is being installed, it is thus possible to set the distance between the two anchor members to the position desired for the two vertebrae associated with said anchor members.

Advantageously, the second link element comprises a rod and the first link element has a housing suitable for receiving the rod, the first link element including locking means for locking the rod inside the housing in a plurality of positions along the longitudinal direction of the link member.

Advantageously, the system is adapted so that the alignment axis lies between the intermediate portion and the vertebrae.

Thus, when the two vertebrae are subjected to stresses tending to move the two anchor members towards each other in translation along the alignment axis, this organization increases the lever arm involved in the bending moment during bending about one of the deformation axes. The intermediate portion is thus subjected to a larger bending moment and is therefore subjected to increased elastic deformation. This makes it possible to increase the capacity of the spine segment having the arthrodesis to bend about said axis and to create a better stress transition with the non-fixed stages.

Other characteristics and advantages of the invention appear more clearly in the description below of two preferred embodiments given as non-limiting examples.

BRIEF DESCRIPTION OF THE DRAWINGS

In the accompanying drawings:

FIG. 1 is an elevation view of a first embodiment of the osteosynthesis system of the invention fixed to two vertebrae;

FIG. 2 is a cross-section on the plane II—II of the FIG. 1 link member;

FIG. 3 is a fragmentary elevation view of a second embodiment of the osteosynthesis system of the invention fixed to vertebrae; and FIG. 4 is an elevation view partially in axial section of the FIG. 3 link member.

DETAILED DESCRIPTION OF THE INVENTION

With reference to FIGS. 1 and 2, a first embodiment of the osteosynthesis system of the invention for the spinal column serves to make up the osteosynthesis device shown. The system comprises merely first and second anchor members or pedicular screws 2 adapted to be fixed respectively to two mutually adjacent vertebrae 4 in the spinal column of a patient. The system also has a link member 6 adapted to interconnect these two anchor members 2.

Each of the two anchor member 2 has an elongate body 8 of longitudinal axis 10 with a threaded shank 12 of slightly conical shape about the axis 10, tapering towards the free end of the shank and suitable for being anchored in the associated vertebra 4. The elongate body 8 has a head at its end opposite to the free end of the threaded shank 12 and designed to extend outside the vertebra 4 within the body of the patient.

In this case, the link member 6 constitutes a single piece. It comprises first and second fixing portions 16 each in the form of a rectilinear cylindrical rod 17. The two rectilinear cylindrical rods 17 are in alignment with each other sharing a common longitudinal axis 18 which is the longitudinal axis of the link member 6 and the alignment axis of the two rectilinear cylindrical rods 17.

Each fixing portion 16 is adapted to be fixed rigidly to the head of one of the anchor members using known means. The axis 18 of the link member is then substantially perpendicular to the longitudinal axis 10 of the anchor member 2. While the osteosynthesis system is being installed, each anchor member 2 is anchored in the associated vertebra 4, and then the anchor members 2 are fixed rigidly to the link member 6.

The link member 6 also has a junction part 28 contiguous with the two fixing portions 16 via one end of each of the rectilinear cylindrical rods 17 and lying on the longitudinal axis 18 between the two rectilinear cylindrical rods. The junction part 28 has an outside face 30 that is generally spherical in shape, with a center of curvature that is situated on the longitudinal axis 18 halfway between the two fixing portions 16.

The junction part 28 has a cylindrical recess 32 passing right through it along a diameter of the sphere. The cylindrical recess 32 has a cylinder axis 34 that intersects the longitudinal axis 18 of the link member halfway between its fixing portions 16 and extending perpendicularly to said longitudinal axis 18.

The junction part 28 also has a notch 36 in the form of a segment of a sphere, being defined by two plane faces 38 of the junction part which face each other, with each of the planes containing the cylinder axis 34 of the cylindrical recess. The notch 36 extends in a radial direction relative to the cylinder axis 34 between the spherical outside face 30 and the cylindrical recess 32. The angle a of this notch as defined about the cylinder axis 34 of the cylindrical recess by the two plane faces 38 is about 15°. One of the plane faces 38 is perpendicular to the longitudinal axis 18 so that the notch lies on one side of the midplane extending transversely to the axis 18 of the link member.

The cylindrical recess 32 and the notch 36 make it possible to distinguish two parts of the junction part 28 extending on either side of the longitudinal axis 18. Thus, the junction part has two abutments 39 extending on a first side of the longitudinal axis 18 associated with the notch 36. Each abutment 39 extends from one of the two respective fixing portions 16 as far as the notch 36, with the facing plane faces 38 constituting two end faces of the abutments. The junction part 28 also has an intermediate portion 40 extending on the second side of the longitudinal axis 18, opposite from the notch 36.

Thus, the two abutments 39 lie on the same side of the intermediate portion 40 as does the longitudinal axis 18. Longitudinal axis 18 passes between the intermediate portion 40 on one side and the two abutments 39 on the other.

The spherical face 30 constitutes an outer face for the abutments 39 and the intermediate portion 40. The spherical faces of the intermediate portion and of the abutments have the same center of curvature. The cylindrical recess 32 defines a cylindrical inner face of the abutments 39 and of the intermediate portion 40.

The intermediate portion 40 is offset laterally relative to the longitudinal axis 18 which is the alignment axis for the two fixing portions 16. The intermediate portion 40 has a neutral fiber 42. The offset is measured in terms of a distance "d" between the neutral fiber 42 and the longitudinal axis 18, and it extends perpendicular to said axis. In this case, this measurement is approximately equal to the diameter of the rectilinear cylindrical rods 17 constituting the fixing portions 16.

The two fixing portions 16 are connected to each other solely via the intermediate portion 40. This portion exerts stresses opposing movement of the two fixing portions 16 in translation along the longitudinal axis 18 towards or apart from each other, and it thus likewise opposes movement of the two anchor members 2. The intermediate portion 40 is elastically deformable about a first deformation axis 45 parallel to the cylinder axis 34 of the cylinder recess 32 and intersecting the intermediate portion level with the neutral fiber 42.

The intermediate portion 40 is also deformable about a second deformation axis 47 perpendicular to the longitudinal axis 18 and to the first deformation axis 45, passing through the center of the sphere and intersecting the first deformation axis 45 and the longitudinal axis 18. The intermediate portion 40 is also elastically deformable about a third deformation axis 49 parallel to the longitudinal axis 18 and perpendicular to the first deformation axis 45, intersecting it on the neutral fiber of the intermediate portion. The second and third deformation axes 47 and 49 pass through the intermediate portion 40. The three deformation axes 45, 47, and 49 are mutually perpendicular, and intersect at a common point to form a frame of reference.

While the system is being installed, the link member 6 is positioned about its longitudinal axis 18 so that the abutments 39 are on its side adjacent to the vertebrae 4, the intermediate portion 40 being on its side remote from the vertebrae 4. Thus, the first deformation axis 45 extends perpendicularly to the longitudinal axis 10 of the anchor members 2, and the second deformation axis 47 is substantially parallel to the axes 10. The intermediate portion 40 is adapted to bend about each of the three deformation axes so as to support at least a fraction of the stresses that are normally exerted on the disk situated between the two vertebrae 4. This bending takes place about one or more of these axes simultaneously.

The two abutments 39 come into abutment against each other when the intermediate portion 40 has bent around the first deformation axis 45 through an angle a equal to a predetermined limit value associated with the shape of the junction part 28 and in the direction of rotation corresponding to the two abutments moving towards each other. This prevents the link member 6 deforming through an angle greater than the predetermined value.

This system provides a flexible arthrodesis between the two vertebrae.

FIGS. 3 and 4 show a second embodiment of the osteosynthesis system of the invention in which the various elements are given references plus one hundred.

This system also has a third anchor member (not shown) extending to the right of the device as visible in FIG. 3. Each of the three anchor members is identical to the anchor members of the first embodiment. The link member 106 has a junction part 128 now comprising a first link member 106a and a second link member 106b that are distinct from each other.

The second link member 106b has an elongate rigid rod 144 of circular section extending in rectilinear manner along the longitudinal axis 18. The second and third anchor members are fixed to the second link member 106b in the same way as in the first embodiment. The second link member 106b has, in particular, a second fixing portion 16.

The first link member 106a has a first fixing portion 16 identical to the first fixing portion in the first embodiment. Adjacent to one end of the fixing portion, it also has an intermediate portion 40 and two abutments 39. The first link member 106a also has a cylindrical sleeve 146 with a cylindrical outer face 148 having the same radius as the radius of curvature of the spherical face 30 and a cylindrical inner face 150. The fixing portion 16 and the cylindrical sleeve 146 share the longitudinal axis 18 of the link member 106. The cylindrical outer 148 extends from and in continuity with the spherical face 30, longitudinally and away from the fixing portion 16. Thus, the outer face of one of the abutments 39 and a portion of the outer face of the intermediate portion 40 are cylindrical in shape. The cylindrical inner face 150 of the cylindrical sleeve 146 is of a radius that is slightly greater than the radius of the elongate rigid rod 144 of the second link member 106b. This cylindrical inner face 150 defines a housing suitable for receiving the elongate rigid rod 144.

The wall of the cylindrical sleeve 146 has a cylindrical duct 153 passing through it on an axis 151 perpendicular to the longitudinal axis 18 of the cylindrical sleeve and opening out in the cylindrical outer face 148 and the cylindrical inner face 150 of the cylindrical sleeve 146. The cylindrical duct 153 is threaded and the second link element 106b has a screw 152 adapted to be engaged in the cylindrical duct 153 to come into abutment against the elongate rigid rod 144 in the cylindrical inner face 150 in order to lock the rod in the housing in a plurality of selectable positions along the longitudinal axis 18. The elongate rigid rod 144, the cylindrical inner face 150, and the screw 152 thus constitute means for fixing the two link members 106a and 106b together, while also enabling the distance between the two fixing portions 16 to be adjusted along the longitudinal axis 18.

To install the osteosynthesis device, the three anchor members are fixed to the vertebrae 4, the elongate rigid rod 144 of the second link member 106b is engaged in the housing 150 of the first link member 106a without tightening the screw 152 so that the elongate rigid rod 144 remains free to slide in the housing along the longitudinal axis 18. The link member 106 is put into place and each of the three anchor members are fixed to the link member 106. Thereafter, the position of the elongate rigid rod 144 in the cylindrical inner face 150 is selected as a function of the desired position along the longitudinal axis 18 for the adjacent vertebra 4 associated with the first link member 106a relative to the vertebra 4 associated with the second link member 106b. These two members are then locked relative to each other by tightening the screw 152 against the elongate rigid rod 144.

The elongate rigid rod 144 constitutes a portion of the link member 106 that is adapted to connect the third anchor member rigidly to the second rigid member. The three anchor members are interconnected by the link member 106.

The various parts of the osteosynthesis system are made of biocompatible alloy, for example.

In each of these two embodiments, the spinal column of the patient is provided with two osteosynthesis systems that are disposed symmetrically on either side of a longitudinal midplane of the spine by being fixed to the same vertebrae.

The maximum amplitude of bending is typically 2° about the third deformation axis 49 (twisting) and 5° to 6° about the second deformation axis 47 (lateral bending).

Naturally, numerous modifications can be made to the invention without going beyond the ambit thereof. The link member 6 of the first embodiment which is of fixed length could be adapted to be associated with at least three anchor members. Conversely, the link member 106 of the second embodiment which is of variable length could be adapted to be associated with only two anchor members.

The system may have more than three anchor members. In particular, a single link member may include one or more (one-piece) junction parts 28 and/or one or more junction parts 128 made up of two distinct elements, each junction part being designed to extend between two anchor members. Advantageously, the link member has a single one-piece junction part 28 at one end, followed by a plurality of two-element junction parts 128.

The center of curvature of the spherical face of the intermediate portion and/or the center of curvature of the spherical faces of the abutments can be situated other than on the cylindrical axis 34 of the cylindrical recess 32.

Independently of whether abutments are present or absent, it is possible, more generally, to provide an osteosynthesis system for the spinal column that comprises at least first, second, and third anchor members adapted to be fixed to first, second, and third respective vertebrae of the spinal column, and a link member (in one or more parts) adapted to interconnect the second and third anchor members rigidly and adapted to interconnect the first and second anchor members so as to exert stresses against the first and second anchor members moving in translation towards each other and being elastically deformable in bending about at least one deformation axis between the first and second anchor members.

Thus, when the first and second vertebrae are subjected to stresses tending to displace the first and second anchor members relative to each other in rotation about the deformation axis, the link member is subjected to a bending moment and bends elastically about the deformation axis. It thus supports the stresses in part. The system partially recreates the biomechanical system of the functional unit made up of the fixed first and second vertebrae together with the intervertebral disk, thereby making it possible to attenuate the amount of stress transferred to the disk underlying the fixing. The system having three anchor members with two anchor members rigidly connected to each other and two anchor members connected to each other by the deformation portion of the link member and located at the end of the series provides a transition or gradient of stiffness between the rigid portion of the spine and its free portion. Consequently, a better distribution of stresses is obtained along the spine.

Such an osteosynthesis system, when it relates to at least three interconnected vertebrae, serves to avoid any sudden discontinuity in stress distribution appearing between the last vertebra of the rigid series and the first free vertebra, and on the contrary, favors harmonious distribution of stresses along the spine.

What is claimed is:

1. An osteosynthesis system for the spinal column, the system comprising at least two anchor members (2) adapted to be fixed to two vertebrae (4) of the spinal column, and a link member (6; 106) adapted to interconnect the two anchor members in translation towards each other, the link member (6; 106) being elastically deformable in bending about at least one deformation axis (45, 47, 49), the link member (6; 106) having at least two fixing portions (16) adapted to be fixed to the two anchor members (2), and at least one intermediate portion, the intermediate portion being offset from an alignment axis defined by the two fixing portions (16), wherein for at least one intermediate portion the link member (6; 106) further has two abutments (39) facing each other and disposed so as to come into abutment against each other when the link member is deformed about at least one deformation axis, in a given direction of rotation and through an angle (a) equal to a predetermined limit value.

2. A system according to claim 1, wherein at least one of the deformation axes extends perpendicularly to a longitudinal direction (10) of each anchor member (2) and to a longitudinal direction (18) of the link member (6; 106).

3. A system according to claim 1, wherein at least one of the deformation axes extends substantially parallel to a longitudinal direction (10) of each anchor member (2) and to a longitudinal direction (18) of the link member (6; 106).

4. A system according to claim 1, wherein at least one of the deformation axes extends parallel to a longitudinal direction (18) of the link member (6; 106).

5. A system according to claim 1, wherein the alignment axis lies between the intermediate portion (40) and the two abutments (39).

6. A system according to claim 1, wherein the intermediate portion (40) has an outer surface (30) of spherical shape.

7. A system according to claim 1, wherein each of the two abutments (39) has an outer surface (30) of spherical shape.

8. A system according to claims 6 or 7, wherein the spherical surface (30) of the intermediate portion and the spherical surfaces (30) of the two abutments have a common center of curvature.

9. A system according to claim 1, wherein for at least one pair of fixing portions, the link member (6) has a junction part (28) contiguous with the two fixing portions, the junction part associated with at least one of the pairs of fixing portions being a single piece.

10. A system according to claim 1, wherein for at least one pair of fixing portions the link member (106) has a junction part (128) contiguous with the two fixing portions, the junction part associated with at least one of the pairs of fixing portions having first and second mutually distinct link elements (106a, 106b) and fixing means for fixing the first and second link elements together.

11. A system according to claim 10, wherein the fixing means are adapted to enable the distance between the two associated anchor members (2) to be adjusted in the longitudinal direction (18) of the link member (106).

12. A system according to claim 11, wherein the second link member (106b) comprises a rod (144) and the first link member (106a) has a housing suitable for receiving the rod, the first link member (106a) including locking means (152) for locking the rod inside the housing in a plurality of positions along the longitudinal direction (18) of the second link member.

13. A system according to claim 1, wherein it is adapted so that the alignment axis lies between the intermediate portion (40) and the vertebrae (4).

* * * * *